(12) United States Patent
Miller

(10) Patent No.: US 8,492,339 B2
(45) Date of Patent: Jul. 23, 2013

(54) ANGIOGENESIS PROMOTED BY CAGED GROWTH FACTORS

(75) Inventor: Seth Adrian Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 509 days.

(21) Appl. No.: 12/605,744

(22) Filed: Oct. 26, 2009

(65) Prior Publication Data

US 2011/0097301 A1  Apr. 28, 2011

(51) Int. Cl.
*A61K 38/00* (2006.01)

(52) U.S. Cl.
USPC ........................................................ 514/13.3

(58) Field of Classification Search
None
See application file for complete search history.

(56) References Cited

U.S. PATENT DOCUMENTS

| | | | |
|---|---|---|---|
| 5,258,453 | A | 11/1993 | Kopecek et al. |
| 5,925,012 | A | 7/1999 | Murphy-Chutorian et al. |
| 5,998,580 | A | 12/1999 | Fay et al. |
| 6,107,466 | A | 8/2000 | Hasan et al. |
| 6,281,015 | B1 | 8/2001 | Mooney et al. |
| 6,337,198 | B1 | 1/2002 | Levene et al. |
| 6,524,274 | B1 | 2/2003 | Rosenthal et al. |
| 6,541,022 | B1 | 4/2003 | Murphy et al. |
| 6,748,954 | B2 | 6/2004 | Lee et al. |
| 6,767,928 | B1 | 7/2004 | Murphy et al. |
| 6,894,161 | B2 | 5/2005 | DesJardins et al. |
| 7,186,413 | B2 | 3/2007 | Bouhadir et al. |
| 7,575,759 | B2 | 8/2009 | Murphy et al. |
| 2003/0191458 | A1 | 10/2003 | Diamond et al. |
| 2004/0247527 | A1 | 12/2004 | Spangler et al. |

FOREIGN PATENT DOCUMENTS

| | | |
|---|---|---|
| WO | WO 96/23543 | 8/1996 |
| WO | WO-2005/056025 | 6/2005 |

OTHER PUBLICATIONS

International Search Report and Written Opinion for PCT/US2010/052817 mailed Feb. 3, 2011, 9 pages.
Chen, R. R. et al., "Polymeric Growth Factor Delivery Strategies for Tissue Engineering", *Pharmaceutical Research*, Aug. 2003, vol. 20, No. 8, pp. 1103-1112.
Richardson T. P. et al., "Polymeric system for dual growth factor delivery," *Nature Publishing Group*, Nov. 2001, vol. 19, pp. 1029-1034.
Ellis-Davies, G. C. R., "Caged Compounds: photorelease technology for control of cellular chemistry and physiology", *Nature Publishing Group*, Aug. 2007, vol. 4, No. 8, pp. 619-628.
Johnson, J. A. et al., "Synthesis of Photocleavable Linear Macromonomers by ATRP and Star Macromonomers by a Tandem ATRP-Click Reaction: Precursors to Photodegradable Model Networks", *American Chemical Society*, Mar. 2007, vol. 40, pp. 3589-3598.
Frechet, J.M.J. et. al., "Chemically Amplified Imaging Materials based on Acid-Catalyzed Reactions of Polyesters or Electrophilic Crosslinking Processes," Journal of Photopolymer Science and Technology, 1990, vol. 3, No. 3, pp. 235-247.
International Preliminary Report on Patentability on PCT/US2010/052817, issued May 1, 2012.
Andreopoulos, F.M. et al., "Delivery of Basic Fibroblast Growth Factor (bFGF) from Photoresponsive Hydrogel Scaffolds," Biomaterials, 2006, vol. 27, pp. 2468-2476.
Delong, S.A. et al., "Covalently immobilized gradients of bFGF in hydrogel scaffolds for directed cell migration," Biomaterials, 2005, vol. 26, pp. 3227-3234.

*Primary Examiner* — Michael Pak
(74) *Attorney, Agent, or Firm* — Foley & Lardner LLP

(57) ABSTRACT

The present disclosure relates to controlling the release of growth factors for the promotion of angiogenesis. The growth factors or a polymer matrix are modified by photoactive compounds, such that the growth factors are not released into an active form until they are irradiated with light. The disclosure also relates to tissue engineering scaffolds comprising one or more polymers and at least two growth factors.

12 Claims, No Drawings

ANGIOGENESIS PROMOTED BY CAGED GROWTH FACTORS

TECHNICAL FIELD

This disclosure relates generally to the fields of vascularization and tissue engineering, including scaffolds.

BACKGROUND

The following description is provided to assist the understanding of the reader. None of the information provided or references cited is admitted to be prior art to the present invention.

Blood vessels are assembled by two processes known as vasculogenesis and angiogenesis. In vasculogenesis, a primitive vascular network is established during embryonic development from endothelial cell precursors called angioblasts. Angiogenesis involves preexisting vessels sending out capillary buds or sprouts to produce new vessels. Angiogenesis is an important process critical to chronic inflammation and fibrosis, to tumor cell growth, and to the formation of collateral circulation. Angiogenesis is involved in the normal process of tissue repair.

Tissue engineering involves the use of living cells to develop biological substitutes for tissue replacement. However, in order for tissue engineering to be practical, scaffolds must be developed that allow for tissue growth that approximates natural tissue growth. Vascularization is necessary to enable tissue engineering to be used in applications that require structures greater than 0.5 mm thick. The controlled growth of vascular networks requires the timed release of multiple growth factors throughout the maturation process. In vivo, the relative timing, quantity, and location of growth factor release is regulated as part of a complex biological system.

SUMMARY

The present disclosure relates to controlling the release of growth factors for the promotion of angiogenesis. In one aspect, the disclosure provides a method for promoting angiogenesis at a target site in a mammalian subject comprising administering to a mammalian subject a formulation comprising at least two growth factors, wherein a first growth factor is released in a bioactive state in response to a first spectral sensitivity range and a second growth factor is released in a bioactive state in response to a second spectral sensitivity range; irradiating the target site with a first wavelength of light in the first spectral sensitivity range to release the first growth factor; and irradiating the target site with a second wavelength of light in the second spectral sensitivity range to release the second growth factor; wherein the sequential administration of the first growth factor and the second growth factor promotes angiogenesis at the target site.

In one embodiment, one or more of the at least two growth factors are caged. In one embodiment, one or more caged growth factors are not released in a bioactive state until radiated.

In one embodiment, the formulation further comprises one or more polymers. In illustrative embodiments, the one or more polymers are selected from the group consisting of poly(lactic acid)polymers, poly(glycolic acid)polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polylactic acid (PLA), polyglycolic acids (PGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), and polyorthoesters or a co-polymer formed from at least two members of the group.

In an illustrative embodiment, the one or more polymers comprise a photoactive group that cleaves the polymer in response to light thereby releasing a growth factor entrained therein. In one embodiment, the one or more polymers comprise a group sensitive to degradation by a photoacid.

In one embodiment, the first and second spectral sensitivity ranges are not substantially overlapping. In one embodiment, an amplitude of the irradiating of the target site controls a rate of release of the first growth factor, the second growth factor, or both. In one embodiment, the irradiating comprises illumination with a laser, a mercury bulb, or an electromagnetic radiation source in combination with a filter.

In one embodiment, the at least two growth factors are independently selected from the group consisting of: transforming growth factor-alpha (TGF-α), transforming growth factor-beta (TGF-β), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor. In an illustrative embodiment, the first growth factor is VEGF and the second growth factor is PDGF.

In one aspect, the disclosure provides a tissue engineering scaffold comprising: one or more polymers and at least two growth factors, wherein a first polymer is configured to release a first growth factor in a bioactive state in response to a first spectral sensitivity range and a second polymer is configured to release a second growth factor in a bioactive state in response to a second spectral sensitivity range.

In one embodiment, the scaffold further comprises collagen. In one embodiment, the scaffold further comprises elastin.

In one aspect, the disclosure provides a method of controlling the release of two or more growth factors at a target site, comprising: delivering a tissue engineering scaffold to a target site; releasing a first growth factor at the target site by radiation of the target site with a first wavelength of light in the first spectral sensitivity range; and releasing a second growth factor at the target site by radiation of the target site with a second wavelength of light in the second spectral sensitivity range. In one embodiment, an amplitude of the radiation of the target site controls a rate of release of the first growth factor, the second growth factor, or both.

In one aspect, the disclosure provides a method for tissue engineering in a mammal, comprising: applying to a tissue progenitor site of a mammal an effective amount of a scaffold comprising one or more polymers and at least two growth factors, wherein a first polymer is configured to release a first growth factor in a bioactive state in response to a first spectral sensitivity range and a second polymer is configured to release a second growth factor in a bioactive state in response to a second spectral sensitivity range.

In one embodiment, the scaffold further comprises a population of cells. In one embodiment, the scaffold comprises a population of vascular endothelial cells or cell precursors and wherein application of the scaffold to the tissue progenitor site stimulates vascularization in the site.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification. As used herein, unless otherwise stated, the singular forms "a," "an," and "the" include plural reference. Thus, for example, a reference to "a polymer" includes a one or more polymers.

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "bioactive state" refers to the form of a compound or agent which is capable of inducing a desired biological or pharmacological effect, which may include but is not limited to angiogenesis. The effect may be local, such as providing for a local neovascular effect in a target site for tissue repair.

As used herein, the term "caged growth factor" refers to a growth factor whose biological activity is controlled by light, typically by the photolytic conversion from an inactive to an active form.

As used herein, the term "biocompatible polymer" refers to a synthetic or natural material that is compatible (i.e., non-toxic) to biological systems. A "biodegradable, biocompatible polymer" refers to a biocompatible polymer that will degrade (i.e., break down) when exposed to, or placed in, a biological system. The rate of degradation may be fast (e.g., degradation may take place in minutes) or slow (e.g., degradation may take place over hours, days, weeks or months), or the polymer may degrade in response to a particular stimulus, e.g., irradiation with light. In some embodiments, the rate of degradation may be controlled by the type of polymer used and/or the amplitude of light applied to the polymer.

As used herein, the term "effective amount" refers to a quantity sufficient to achieve a desired therapeutic effect, e.g., an amount of a growth factor which results in angiogenesis in a target tissue. The amount of a composition administered to the subject will depend on characteristics of the individual, such as general health, age, sex, body weight and tolerance to drugs. The skilled artisan will be able to determine appropriate dosages depending on these and other factors. The compositions can also be administered in combination with one or more additional therapeutic compounds.

As used herein, the term "irradiation" or "irradiating" is used expansively to encompass bombardment of the target site with photons, e.g. visible light, ultraviolet ("UV") radiation, combinations thereof, and the like, in order to effect conversion of a photosensitive material.

As used herein, the term "polymer" refers to a macromolecule made of repeating (monomer) units or multimers.

As used herein, the term "spectral sensitivity range" refers to the spectral regions in which a photosensitive material is structurally transformed or changed in response to radiation.

As used herein, the term "tissue scaffold" refers to any composition formed into a porous matrix into which tissue can grow in three dimensions.

As used herein, the terms "scaffolding polymers" or "scaffolding materials" refer to the materials used to make tissue scaffolds. The terms refer to both monomeric units of the materials and the polymers made therefrom. Scaffolding polymers may be biodegradable or non biodegradable.

Overview

Vascularization is a complex process that is regulated by multiple growth factors, which are each released at different times during the maturation of a blood vessel. These timings will not be identical for blood vessels of different sizes, and at different locations in a tissue engineering construct. The compositions and methods described herein allow for the release of multiple growth factors to be regulated in time and space.

The molecular mechanisms controlling the formation of mature vasculature involve several sequential factors, each playing a distinct role. Controlled delivery of at least two growth factors (e.g., VEGF and PDGF) initiates formation of a blood vessels and induces their maturation. Thus, therapeutic angiogenesis benefits from the actions at least two types of molecules: initiation of blood vessels, as provided by VEGF or other factors (e.g., angiopoietin-2), and the maturation of blood vessels by PGDF or other factors (e.g., angiopoietin-1). In one embodiment, separate controlled release formulations of VEGF and PDGF are created, such that VEGF is released before PDGF.

Thus, in one aspect, the present disclosure relates to controlling the release of growth factors for the promotion of angiogenesis. In illustrative embodiments, either the growth factors or the polymer matrix are modified by photoactive compounds, such that the growth factors are not released until they are irradiated with light. This approach allows for control of (1) the timing, (2) the location, and (3) the amount of growth factor release. More than one growth factor can be released by irradiation, e.g., each by a separate wavelength, allowing for the release of multiple chemicals to proceed with multiple timings at different locations. Spatial control of growth factor release can be important, as different regions in a tissue engineering construct may mature at different rates due to differences in mass transport. Existing methods that rely on standard controlled release of drugs cannot accommodate this variability.

In some embodiments, growth factors may be released in a desired space by irradiating the region with light. The timing of the release is thus controlled by determining when the irradiation starts, the rate of release is controlled by modulating the amplitude of the irradiation, and the location of the release is determined by focusing and/or masking the incoming light. For instance, each growth factor may be released using different photoactive molecules, having non-overlapping absorbances. As a result, the disclosure enables control over the release kinetics of multiple growth factors at different rates in overlapping regions of space.

In one embodiment, the growth factors themselves can be "caged", or derivitized with a molecule such that they are not released in a bioactive state until irradiated. In another embodiment, the growth factors are entrained within a photosensitive polymer, which may be degraded in response to exposure to light, thereby releasing the growth factor. Thus, in the first embodiment, the growth factor itself is activated in response to light; in the second embodiment, a capsule or polymer containing the growth factor is exposed to light, thereby releasing an active growth factor.

In one embodiment, two growth factors (e.g., VEGF and PDGF) are entrained in a photodegradable polymer by derivatizing two sets of high molecular weight biocompatible polymer (e.g., PLA) with two different photoactive groups; encapsulating the growth factors in each of the two polymers to form two separate powders; and fusing the powders together to form a porous tissue engineering scaffold.

In one embodiment, three growth factors are entrained in a photodegradable polymer according to the following method: derivatizing three sets of high molecular weight biocompatible polymer (e.g., PLA) with three different photoactive groups of orthogonal photoactivity; encapsulating three separate growth factors in each of the three polymers, in order to form three separate powders; and fusing the powders together to form a porous tissue engineering scaffold.

These powders can be optionally supplemented by a conventional molecular weight polymer of the same chemical composition, to dilute the total amount of encapsulated material. After cell seeding, immature vascular networks will be physically surrounded by all three growth factors, but none will be released until stimulated with the appropriate wavelength of light.

Caged Growth Factors

One embodiment is directed to a growth factor bonded to a photoreactive moiety. The resulting conjugate can be selectively cleaved to release the active growth factor. Cleavage, as referred to herein, is by photocleavage or a cleavage event triggered by the application of radiation to the conjugate.

In some embodiments, the photoreactive moiety is a chemical moiety capable of interacting directly or indirectly with a therapeutic agent which can be cleaved with electromagnetic radiation. The photoreactive moiety may be positioned on the therapeutic agent (e.g., growth factor) so as to interfere with or prevent the normal biological activity of the agent. For instance, in the case of a polypeptide, the photoreactive moiety may be positioned near the active site or substrate binding domain of the protein, which blocks the activity of the polypeptide. Suitable photoreactive moieties are generally selected for absorption of light that is deliverable from common radiation sources (e.g. UV light ranging from 240-370 nm). Examples of photoreactive moieties which are photoresponsive to such wavelengths include, but are not limited to, acridines, nitroaromatics and arylsulfonamides.

The efficiency and wavelength at which the photoreactive moiety becomes photoactivated and thus releases or "uncages" the therapeutic agent will vary depending on the particular functional group(s) attached to the photoreactive moiety. For example, when using nitroaromatics, such as derivatives of o-nitrobenzylic compounds, the absorption wavelength can be significantly lengthened by addition of methoxy groups. In one embodiment, nitrobenzyl (NB) and nitrophenylethyl (NPE) is modified by addition of two methoxy residues into 4,5-dimethoxy-2-nitrobenzyl (DMNB) and 1-(4,5-dimethoxy-2-nitrophenyl)ethyl (DMNPE), respectively, thereby increasing the absorption wavelength range to 340-360 nm ($\lambda_{max}$=355 nm).

In one embodiment, the photoreactive moiety is a 2-nitrobenzyl derivative. In their ground state, 2-nitrobenzyl-based agents and conjugates have an intramolecular hydrogen bond between benzylic hydrogen and the ortho nitro group. Upon illumination with wavelengths of greater than 300 nm, these chemical compounds transition to an excited state. Proton transfer reaction from benzylic carbon to the oxygen in nitro group takes place which is followed by electron rearrangement. This reaction results in the formation of a transient species called an aci-nitro ion which is in a rapid equilibrium with a cyclic form. In the cyclic intermediate, electron rearrangement and oxygen transfer from nitrogen to benzylic carbon takes place resulting in the formation of 2-nitroso derivatives and release of a substrate which is a good leaving group.

In one embodiment, the photocleavable moiety is 3,5-dimethoxybenzyl or 2-nitrobenzenesulfenyl. These nitrobenzyl groups all contain a benzylic carbon-hydrogen bond ortho to a nitro group, which is necessary for their photolability.

In one embodiment, the photoreactive moiety is a photocleavable biotin (PCB). A wide variety of biotinyl moieties can be used to form a PCB molecule. Biotin is comprised of a ring linked to an alkyl chain terminated by a carboxyl group. Numerous modifications can be made to the biotin moiety which involve changes in the ring, spacer arm and terminating group, all of which still exhibit a high affinity for streptavidin, avidin and their derivatives. Examples of photocleavable biotins are known in the art. Unlike conventional biotins, photocleavable biotins enable one to release or elute the bound substrate from the immobilized avidin, streptavidin or their derivatives in a completely unmodified form. Once the biotin is photocleaved from a protein or protein/binding complex, all the native properties and function will be restored to its native form for further use and characterization. Choice of photolabile group and/or spacer arm depends on the target growth factor including to which the photocleavable moiety is to be attached. It also depends on the exact conditions for photocleavage.

Photocleavage of conjugates should typically not damage the released therapeutic agent or impair the agent's activity. Proteins, nucleic acids and other protective groups used in peptide and nucleic acid chemistry are known to be stable to most wavelengths of radiation above 300 nm. The yield and exposure time necessary for release of substrate photo-release are strongly dependent on the structure of photoreactive moiety. For instance, illumination times may vary from about 1 minute to about 24 hours, less than 4 hours, less than two hours, and less than one hour, and yields may be between about 1% to about 95%. In some embodiments, the illumination times are from about 10 seconds to about 5 minutes, from about 30 seconds to about 5 minutes, from about 1 minute to about 10 minutes, from about 5 minutes to about 30 minutes, or from about 30 minutes to about 90 minutes.

Another embodiment is directed to caged growth factors which are pharmaceutical compositions. Compositions must be safe and nontoxic and can be administered to patients such as humans and other mammals. Compositions may be mixed with a pharmaceutically acceptable carrier such as water, oils, lipids, saccharides, polysaccharides, glycerols, collagens and combinations thereof and administered to patients.

In one embodiment, after general administration of the composition to the patient, the site to be treated is exposed to appropriate radiation releasing substrate which produces a therapeutic response in a patient. Uncoupling from the bioreactive agent at the point of maximal biological effect is an advantage unavailable using current administration or stabilization procedures. In an analogous fashion, other areas of the patient's body may be protected from the biological effect of the pharmaceutical agent. Consequently, using these conjugates, site-directed and site-specific delivery of a pharmaceutical agent is possible.

Polymers and Tissue Scaffolds with Entrained Growth Factors

Tissue scaffolds provide a matrix for cells to guide the process of tissue formation in vivo in three dimensions. Synthetic polymers are attractive scaffold materials as they can be readily produced with a wide range of reproducible properties and structures. Polymer tissue scaffolds also provide mechanical support against compressive and tensile forces, thus maintaining the shape and integrity of the scaffold in the environment in which the tissue is implanted.

The morphology of the tissue scaffold can guide the structure of an engineered tissue, including the size, shape and vascularization of the tissue. The proper design of these tissue scaffolds allows them to exhibit the required range of mechanical and biological functions. Synthetic polymeric materials can be precisely controlled in material properties and quality. Moreover, synthetic polymers can be processed with various techniques and supplied consistently in large quantities. The mechanical and physical properties of synthetic polymers can be readily adjusted through variation of molecular structures so as to fulfill their functions without the use of either fillers or additives.

In one embodiment, a photolabile group that cleaves (or accelerates the cleavage of) a polymer can be used to release a growth factor that is associated with or encapsulated within a polymer. This is accomplished by incorporation of photoactive groups in the polymer backbone, or by inclusion of photoacids in the polymer formulation. One advantage of this approach is that derivitization or reformulation of a polymer with a photoactive compound is relatively simpler and cheaper than caging multiple growth factors (each demanding a separate synthesis), and such polymer can be generalized for use in other systems.

A variety of synthetic biodegradable polymers can be utilized to fabricate tissue scaffolds. In general, these materials are utilized as structural elements in the scaffold. Poly(glycolic acid) (PGA), poly(lactic acid) (PLA), Poly lactic co-lactic acid (PLLA) and poly(lactic acid)-poly(glycolic acid) (PLGA) polymers are commonly used synthetic polymers in tissue engineering. These polymers are also extensively utilized in other biomedical applications such as drug delivery and are FDA approved for a variety of applications. A number of PGA, PLA, PLLA and PLGA and other synthetic polymer tissue scaffolds are known in the art.

The tissue scaffolds may also include natural polymer materials, such as collagen. Type I collagen may also be combined with glycosaminoglycans to form gels which mimic native dermal tissue. A variety of other ECM molecules, including laminin, have been utilized as cell delivery tissue scaffolds, and any such tissue scaffold may be used in the context of the present disclosure.

In illustrative embodiments, the polymer used in the tissue scaffold is a polymer of lactic acid. Polymers and copolymers of lactic acid are transparent, colorless thermoplastics with a wide range of physical properties that mimic those of many conventional thermoplastics. When exposed to moisture or biological fluids, these modified plastics hydrolyze slowly, over a period of several months to natural, harmless, materials such as lactic acid. The copolymers of lactic acid and glycolic acid were originally developed and marketed as an industrial product as resorbable sutures. These polymers and copolymers have high strength and biocompatibility and have controlled degradability.

Poly(lactic acid) and poly(glycolic acid) can be prepared by either condensation polymerization of the free acids or by catalytic, ring-opening polymerization of the dilactones. Both polylactic acid and polyglycolic acid are environmentally compatible because they degrade respectively to lactic acid and glycolic acid, both natural harmless products. While these polymers degrade primarily by hydrolysis, with the addition of certain other materials, they may degrade also by exposure a other source of light, e.g., UV light. The physical properties such as crystallinity, melting point, degradation rate, elasticity and the like can be varied depending upon the amount and the type of copolymer formed.

Incorporation of photoactive compounds into polymer matrix can be accomplished by the host-guest approach, as well as via chemical bonding of the photoactive compounds to the polymeric backbone. In one embodiment, the photoactive compound that is incorporated into the polymer matrix is a keto-containing monomer, which loses CO on irradiation with UV light, in order to fragment the polymer. For example, the keto-containing monomer may be a 3-pentanone, such as 1,5-bis(4'-methoxycarbonylphenyl)-3-pentanone. In some embodiments, the ketone is present in the polymer in an amount of 0.1-100 mole percent, 0.1-15 mole percent, or 1.0-5 mole percent of the repeating units. In another embodiment, the photosensitive monomer is a methylene butyrolactone derivative. Further examples of photoactive compounds that may be incorporated into polymer matrix are described in U.S. Pat. Nos. 3,878,169; 4,883,857; U.S. Pat. No. 5,395,692; and U.S. Pat. No. 5,434,236.

Degradation of the polymers may also be induced by a photoacid. Compounds producing acids upon illumination with light are called photoacid generators. There are two major groups of acid generators: ionic and non-ionic ones. One suitable group of ionic acid generators consists of onium salts containing metal halides ($BF_4^-$, $SbF_6^-$, $AsF_6^-$ or $PF_6^-$). In one embodiment, the photoacid isaryldiazonium. Upon irradiation with UV light in the range of about 190-300 nm, the onium salts photoproduce a protic acid, which may then cleave the polymer backbone and release the entrained growth factor. In some embodiments, the photoacid generators are selected from the group consisting of: (4-Bromophenyl)diphenylsulfonium triflate; (4-Chlorophenyl)diphenylsulfonium triflate; (4-Fluorophenyl)diphenylsulfonium triflate; (4-Iodophenyl)diphenylsulfonium triflate; (4-Methoxyphenyl)diphenylsulfonium triflate; (4-Methylphenyl) diphenylsulfonium triflate; (4-Phenoxyphenyl)diphenylsulfonium triflate; (4-Phenylthiophenyl)diphenylsulfonium triflate; (4-Methylthiophenyl)methyl phenyl sulfonium triflate; (4-tert-Butylphenyl)diphenylsulfonium triflate; (tert-Butoxycarbonylmethoxynaphthyl)diphenylsulfonium triflate; 2-(4-Methoxystyryl)-4,6-bis(trichloromethyl)-1,3,5-triazine; Bis(4-tert-butylphenyl)iodonium p-toluenesulfonate; Bis(4-tert-butylphenyl)iodonium perfluoro-1-butanesulfonate; Bis(4-tert-butylphenyl)iodonium triflate; Boc-methoxyphenyldiphenylsulfonium triflate; Diphenyliodonium 9,10-dimethoxyanthracene-2-sulfonate; Diphenyliodonium nitrate; Diphenyliodonium p-toluenesulfonate; Diphenyliodonium triflate; N-Hydroxy-5-norbornene-2,3-dicarboximide perfluoro-1-butanesulfonate; N-Hydroxynaphthalimide triflate; Triarylsulfonium hexafluorophosphate; Triphenylsulfonium perfluoro-1-butanesufonate; Triphenylsulfonium triflate; Tris(4-tert-butylphenyl)sulfonium perfluoro-1-butanesulfonate; and Tris(4-tert-butylphenyl)sulfonium triflate One aspect of the disclosure incorporates growth factors into the tissue scaffolds or hydrogels to stimulate angiogenesis. It is generally understood that a growth factor that has already been established to have a beneficial physiological effect on a particular cell type should be chosen for use in regenerating tissue containing such cells. Certain growth factors may be used to stimulate the proliferation of a wide number of cell types, whereas other growth factors may have a more limited or defined cell-specificity.

Platelet-derived growth factor, (PDGF, e.g., PDGF-BB), is one member of the TGF supergene family of growth factors. Particular examples of suitable growth factors include other members of the TGF supergene family, such as, BMP-2, BMP 4, BMP-7, VEGF, FGF-1, FGF-2, IGF-1, IGF-2, GDF-1, GDF-2, GDF-2, GDF-3, GDF-4, GDF-5, or combinations of the same. In one embodiment, VEGF and PDGF-BB are effective for the growth of new blood vessels and may be used in the present compositions.

The growth factors or stimulatory agents that are useful in the context of the present disclosure may be purified from natural sources or may be recombinantly prepared proteins. They may be obtained from commercial sources, if desired. Those of skill in the art will know how to obtain and use such growth factors in the context of angiogenesis in light of the present disclosure.

Other Agents Added to Polymers and Tissue Scaffolds

One aspect of the disclosure incorporates additional bioactive agents into the tissue scaffolds or hydrogels to stimulate tissue growth, relieve pain, fight infection, reduce inflammation or otherwise facilitate the process of tissue repair and regeneration.

ECM Components. In some embodiments, the tissue-specific function of the proliferating cells that infiltrate the tissue scaffold should be maintained. The function of the proliferating cells is strongly dependent on the presence of specific growth factors and ECM molecules. For example, in vitro, it is known that cells can be switched from a phase of tissue-specific gene expression to one of proliferation simply by altering the ECM presentation to the cell. Accordingly ECM proteins, hyaluronic acid or other components of the ECM may be incorporated into the tissue scaffolds. If desired, any one of a variety of tissue scaffolds that incorporate specific ECM molecules may be used to supplement the correct signalling to the host's proliferating cells. Synthetic materials that incorporate specific peptides to enhance cell adhesion may be used, including those that incorporate a variety of different peptides in order to mimic the multi-functional nature of ECM molecules.

Antiinflammatory Agents. In certain embodiments, an anti-inflammatory agent is combined with the tissue scaffold or hydrogel implanted into a subject. In one embodiment, the tissue scaffold or hydrogel may include the anti-inflammatory agent alone, while in other embodiments it may include the anti-inflammatory agent in combination with a morphogenic factor, antibiotic or other biologically active agent. Suitable anti-inflammatory agents include, amongst others, those in the class of Cox-I and Cox II inhibitors. Examples of such agents include acetyl-salicylic acid, acetaminophens, naproxen, ibuprofen and the like. Another example of a suitable class of anti-inflammatory agents includes soluble cytokine receptors such as Embrel™ or IL-1b binding receptors. The amount of anti-inflammatory agent used is adjusted so as to be released from the tissue scaffold or hydrogel over a period of about 2 days or more.

Analgesic Agents or Anesthetics. In some embodiments, the tissue scaffold may include analgesic agents or anesthetics. The anti-inflammatory agents mentioned above also serve as analgesic agents, thus analgesic agents include antiinflammatories. In addition, the analgesic agent may include local pain deadening agents (anesthetics) such as lidocaine, that provide local pain relief for a period of about 30 minutes or more.

Antibiotic Agents. In various embodiments, the tissue scaffold may include an antibiotic agent. There are numerous classes of antibiotic agents including, but not limited to: tetracyclines, chemically modified tetracyclines, cyclosporins, those in the penicillin family, amoxcillan, gentamicin, erythromycin, chloramphenicol, florfenicol, vancomycin, everninomicin, cefotaxime, streptomycin, ciprofloxacin, nalidixic acid, bacitracin, enrofloxacin, and flavomycin.

Photorelease of Caged or Polymer-Entrained Growth Factors

In some embodiments, the process of releasing one or more active growth factors is done in a spatially selective manner, which allows for controlled growth of different sized vascular channels at different locations. The timing of release and the rate of release can be modulated by controlling the intensity (i.e., lumens and duration) of irradiation. Lastly, the presently disclosed subject matter allows for improved spatial and temporal control of the release of growth factor. Radiation to promote photorelease of the therapeutic agent can be provided by a variety of sources including, but not limited to, non-coherent UV light sources and excimer sources.

In an illustrative embodiment, the growth factors VEGF and PDGF are entrained within a tissue engineering scaffold. The scaffold includes at least two co-polymers, which are synthesized to different photosensitive monomers, e.g., 5-bis (4'-methoxycarbonylphenyl)-3-pentanone and methylene butyrolactone. One of the polymers encompasses the VEGF and one of the polymers encompasses the PDGF. The scaffold is implanted in a particular body tissue and then radiation of the appropriate wavelength may be applied to degrade the respective photosensitive monomers. Typically, the polymer containing VEGF will be degraded first, followed by the polymer containing PDGF approximately 2-3 weeks later.

In an illustrative embodiment, about 1-100 fmol VEGF per $mm^3$ of tissue is released per day, over the course of 1 week. In a particular embodiment, about 10 fmol VEGF per $mm^3$ of tissue is released per day, over the course of 1 week. The intensity, duration, and frequency of administration of radiation is selected to ensure the desired amount of VEGF is delivered to the target tissue. The PDGF should be released at approximately 2-3 weeks, with a release rate of about 10-100 $fmol/mm^3/day$. In a particular embodiment about 20 $fmol/mm^3/day$ PDGF is released. The intensity, duration, and frequency of administration of radiation is selected to ensure the desired amount of PDGF is delivered to the target tissue.

The determination of the appropriate dosage of radiation required in order to degrade the polymer or activate the growth factor may be accomplished by calibration experiments in which a particular cage or polymer and growth factor combination is tested in vitro using destructive analysis. For example, a particular dosage of radiation is applied to the tissue scaffold and the sample is analyzed to determine the amount of cleavage and/or the amount of growth factor released into the media. The results of the in vitro experiments can be extrapolated to in vivo conditions.

The release of the growth factors in vivo can also be monitored by tissue biopsy in order to examine the quality of tissue maturation, for example by looking at the density of vessels (number per square millimeter) and their size and size distribution. Non-invasive methods for measuring blood vessel density may include angiography or arteriography, and computerized tomography or MRI with radiocontrast dyes (See U.S. Pat. No. 7,011,631).

The radiation applied may comprise one or more wavelengths from the electromagnetic spectrum including x-rays (about 0.1 nm to about 10.0 nm; or about $10^{18}$ to about $10^{16}$ Hz), ultraviolet (UV) rays (about 10.0 nm to about 380 nm; or about $8 \times 10^{16}$ to about $10^{15}$ Hz), visible light (about 380 nm to about 750 nm; or about $8 \times 10^{14}$ to about $4 \times 10^{14}$ Hz), infrared light (about 750 nm to about 0.1 cm; or about $4 \times 10^{14}$ to about $5 \times 10^{11}$ Hz), microwaves (about 0.1 cm to about 100 cm; or about $10^8$ to about $5 \times 10^{11}$ Hz), and radio waves (about 100 cm to about $10^4$ m; or about $10^4$ to about $10^8$ Hz). Multiple forms of radiation may also be applied simultaneously, in combination or coordinated in a step-wise fashion. Radiation exposure may be constant over a period of seconds, minutes or hours, or varied with pulses at predetermined intervals.

Typically, the radiation source is placed at a specified distance from the conjugate or polymer to be irradiated. That distance may be empirically determined or calculated from the energy loss produced between the source and the target and the amount of energy emitted by the source. In one embodiment, the radiation applied is UV, visible or IR radiation of the wavelength between about 200 nm to about 1,000 nm, between about 260 nm to about 600 nm, or between about 300 nm to about 500 nm. Radiation is administered continuously or as pulses for hours, minutes or seconds, and typically for the shortest amount of time possible to minimize any risk of damage to the substrate or the patient. Radiation may be administered for less than about one hour, less for than about 30 minutes, less than about ten minutes, or less than about one minute. Visible, UV and IR radiation can be conveniently and inexpensively generated from commercially available sources.

Temporal control may be established by modulating the light intensity on the construct. Other methods relying on controlled release of the drugs will use polymers of different formulations to obtain different release rates, and as a result rely on a timing protocol that is set before cell growth begins, and does not take account of current conditions in the construct. This disclosure enables the release of growth factor in response to specific observable biological events, as occurs in native biological systems, and, it allows for optimization of release conditions using a single formulation, and does not limit the release of growth factors to a smooth rate.

To deliver the growth to a specific body region, a drug delivery device can be guided into a position adjacent to the region to be treated, using conventional techniques. After positioning the device adjacent to the region to be treated, the device can be inflated or expanded so that its comes into contact with the surrounding tissue. Light is then transmitted to the target, e.g., by transmission throughout the interior of the device, causing photolytic release of the therapeutic agent into the surrounding tissue.

Suitable medical devices include, for example, balloon catheters, endoscopes, polymer stents, and the like. In one embodiment, a conventional balloon angioplasty catheter containing one or more optical fibers is modified by photoreleasably linking a therapeutic agent to the exterior of the balloon. The catheter is guided into position adjacent to an area to be treated using, for example, a guide wire, and the balloon is then inflated so as to contact and dilate the surrounding tissue. Following inflation of the balloon, radiation from an irradiation source is delivered via one or more optical fibers which extend through the terminal end of the catheter into the balloon. A diffusive radio-opaque tip is optionally attached to the terminal end through which the radiation is delivered and scattered throughout the balloon. The light delivered through the balloon subsequently causes photolytic release of one or more growth factors.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All references cited herein are incorporated by reference in their entireties and for all purposes to the same extent as if each individual publication, patent, or patent application was specifically and individually incorporated by reference in its entirety for all purposes.

Other embodiments are set forth in the following claims.

What is claimed is:

1. A method for promoting angiogenesis at a target site in a mammalian subject comprising:
    administering to a mammalian subject a formulation comprising at least two growth factors, wherein a first growth factor is released in a bioactive state in response to a first spectral sensitivity range and a second growth factor is released in a bioactive state in response to a second spectral sensitivity range;
    irradiating the target site with a first wavelength of light in the first spectral sensitivity range to release the first growth factor; and
    irradiating the target site with a second wavelength of light in the second spectral sensitivity range to release the second growth factor;
    wherein the sequential administration of the first growth factor and the second growth factor promotes angiogenesis at the target site.

2. The method of claim 1, wherein one or more of the at least two growth factors are caged.

3. The method of claim 2, wherein the one or more caged growth factors are not released in a bioactive state until radiated.

4. The method of claim 1, wherein the formulation further comprises one or more polymers.

5. The method of claim 4, wherein the one or more polymers are selected from the group consisting of poly(lactic acid)polymers, poly(glycolic acid)polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polylactic acid (PLA), polyglycolic acids (PGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), and polyorthoesters or a co-polymer formed from at least two members of the group.

6. The method of claim 4, wherein the one or more polymers comprise a photoactive group that cleaves the polymer in response to light thereby releasing a growth factor entrained therein.

7. The method of claim 4, wherein the one or more polymers comprise a group sensitive to degradation by a photoacid.

8. The method of claim 1, wherein the first and second spectral sensitivity ranges are not substantially overlapping.

9. The method of claim 1, wherein the at least two growth factors are independently selected from the group consisting of: transforming growth factor-alpha (TGF-$\alpha$), transforming growth factor-beta (TGF-$\beta$), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor.

10. The method of claim 1, wherein the first growth factor is VEGF and the second growth factor is PDGF.

11. The method of claim 1, wherein an amplitude of the irradiating of the target site controls a rate of release of the first growth factor, the second growth factor, or both.

12. The method of claim 1, wherein the irradiating comprises illumination with a laser, a mercury bulb, or an electromagnetic radiation source in combination with a filter.

* * * * *

UNITED STATES PATENT AND TRADEMARK OFFICE
CERTIFICATE OF CORRECTION

PATENT NO. : 8,492,339 B2  Page 1 of 1
APPLICATION NO. : 12/605744
DATED : July 23, 2013
INVENTOR(S) : Miller It is certified that error appears in the above-identified patent and that said Letters Patent is hereby corrected as shown below:

On the Title Page, item (56), in Column 2, Line 17, delete "et." and insert -- et --, therefor.

In the Specification

In Column 4, Line 30, delete "PGDF" and insert -- PDGF --, therefor.

In Column 8, Line 3, delete "a other" and insert -- to other --, therefor.

In Column 8, Line 30, delete "isaryldiazonium." and insert -- is aryldiazonium. --, therefor.

In Column 9, Line 6, delete "GDF-2, GDF-2," and insert -- GDF-2, --, therefor.

In Column 10, Line 1, delete "amoxcillan," and insert -- amoxicillin, --, therefor.

In Column 11, Line 19, delete "less for than" and insert -- less than --, therefor.

In Column 11, Line 39, delete "its comes" and insert -- it comes --, therefor.

Signed and Sealed this
Twenty-second Day of October, 2013

Teresa Stanek Rea
*Deputy Director of the United States Patent and Trademark Office*